United States Patent [19]
Chorvat et al.

[11] 3,991,061
[45] Nov. 9, 1976

[54] AZANAPHTHALENEACETIC ACID DERIVATIVES

[75] Inventors: Robert J. Chorvat, Arlington Heights; Raphael Pappo, Skokie, both of Ill.

[73] Assignee: G. D. Searle & Co., Chicago, Ill.

[22] Filed: July 16, 1975

[21] Appl. No.: 596,509

[52] U.S. Cl. .................. 260/287 D; 260/287 R; 260/287 T; 260/287 K; 260/289 R; 424/258
[51] Int. Cl.² .............. C07D 217/24; C07D 215/22
[58] Field of Search ................. 260/287 D, 287 R

[56] References Cited
UNITED STATES PATENTS
2,921,939  1/1960  Ramsden ..................... 260/287 R

*Primary Examiner*—Nicholas S. Rizzo
*Assistant Examiner*—David E. Wheeler
*Attorney, Agent, or Firm*—John J. McDonnell

[57] ABSTRACT

The present invention encompasses compounds of the formula

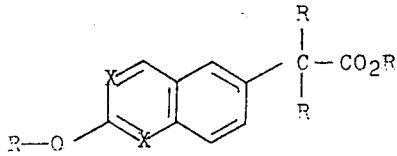

wherein R represents hydrogen or lower alkyl having 1–7 carbon atoms and wherein one X represents (nitrogen) N and the other X represents methylidyne. The compounds of the present invention are prepared by the methods set out in the following scheme:

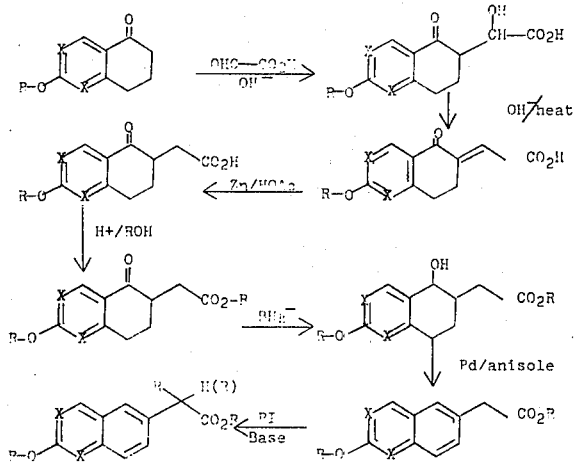

Scheme I wherein R and X are as defined above. Compounds of the present invention are useful anti-inflammatory agents.

7 Claims, No Drawings

AZANAPHTHALENEACETIC ACID DERIVATIVES

The present invention encompasses compounds of the formula

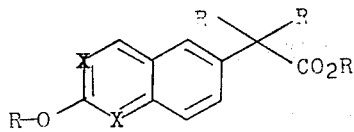

wherein R represents hydrogen or lower alkyl having 1–7 carbon atoms and wherein one X represents a nitrogen atom (N) and the other X represents methylidyne (C—H). Lower alkyl contemplates straight and branched alkyl radicals having 1–7 carbon atoms with methyl and ethyl being the preferred lower alkyls.

Compounds of the formula

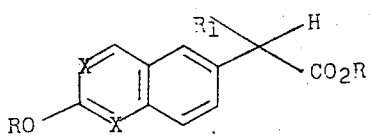

wherein $R_1$ is lower alkyl and R is as earlier defined may have the dl, d, or l stereochemical configuration about the chiral center.

Thus the present invention encompasses compounds of the formula

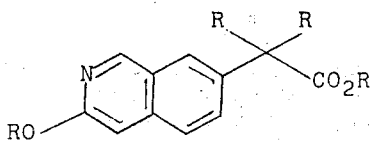

wherein R represents hydrogen and lower alkyl having 1–7 carbon atoms. This embodiment of the present invention is represented by 3-methoxy-2-azanaphthalene-7-acetic acid, ethyl 3-methoxy-2-azanaphthalene-7-acetate, 3-methoxy-2-azanaphthalene-7α-methylacetic acid, 3-methoxy-2-azanaphthalene-7-α,α-dimethylacetic acid, methyl 3-ethoxy-2-azanaphthalene-7-acetic acid, and 3-methoxy-2-azanaphthalene-7-α-methyl-α-ethylacetic acid.

The present invention also encompasses compounds of the formula

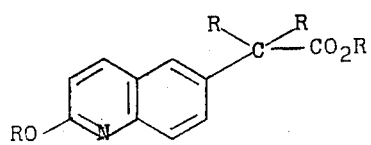

wherein R represents hydrogen or lower alkyl having 1–7 carbon atoms. This embodiment is represented by 2-methoxy-1-azanaphthalene-6-acetic acid, ethyl 2-methoxy-1-azanaphthalene-6-acetate, 2-methoxy-1-azanaphthalene-6-α-methylacetic acid, 2-methoxy-1-azanaphthalene-6-α,α-dimethylacetic acid, and methyl 2-ethoxy-1azanaphthalene-6-α,α-dimethylacetate.

6-Alkoxy-2-naphthyleneacetic acid derivatives are described in British Pat. No. 1,211,134, filed Nov. 4, 1970. The compounds of the present invention are distinguished in that they have a nitrogen atom in the 5 or 7-position.

Compounds of the present invention are useful intermediates for other biologically active compounds. For instance the corresponding aldehydes and alcohols are potent anti-inflammatory compounds. Thus reduction of esters of compounds of the present invention with diisobutylaluminum hydride provides aldehydes of the formula

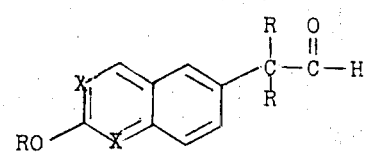

wherein R and X are as previously defined.
This formula encompasses compounds such as:
3-methoxy-2-azanaphthalene-7-acetaldehyde,
3-methoxy-2-azanaphthalene-7-α-methylacetaldehyde,
3-methoxy-2-azanaphthalene-7-α,α-dimethylacetaldehyde,
2-methoxy-1-azanaphthalene-6-acetaldehyde,
2-methoxy-1-azanaphthalene-6-α-methylacetaldehyde,
2-methoxy-1-azanaphthalene-6-α,α-dimethylacetaldehyde, and
2-ethoxy-1-azanaphthalene-6-α-methyl-α-ethylacetaldehyde.

Esters and acids of the present invention as well as the above mentioned aldehydes may be reduced to the corresponding alcohols also having anti-inflammatory activity. These alcohols have the following formula.

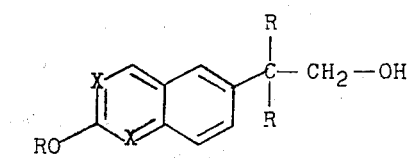

wherein R and X are as previously defined. This formula encompasses alcohols such as:
7-hydroxyethyl-3-methoxy-2-azanaphthalene,
7-(1-hydroxyisopropyl)-3-methoxy-2-azanaphthalene,
7-(1-hydroxy-2-methylisopropyl)-3-methoxy-2-azanaphthalene,
6-hydroxyethyl-2-methoxy-1-azanaphthalene,
6-(1-hydroxyisopropyl)-2-methoxy-1-azanaphthalene, and
6-(1-hydroxy-2-methylisopropyl)-2-methoxy-1-azanaphthalene.

The compounds of the present invention are prepared by the methods set out in Scheme I.

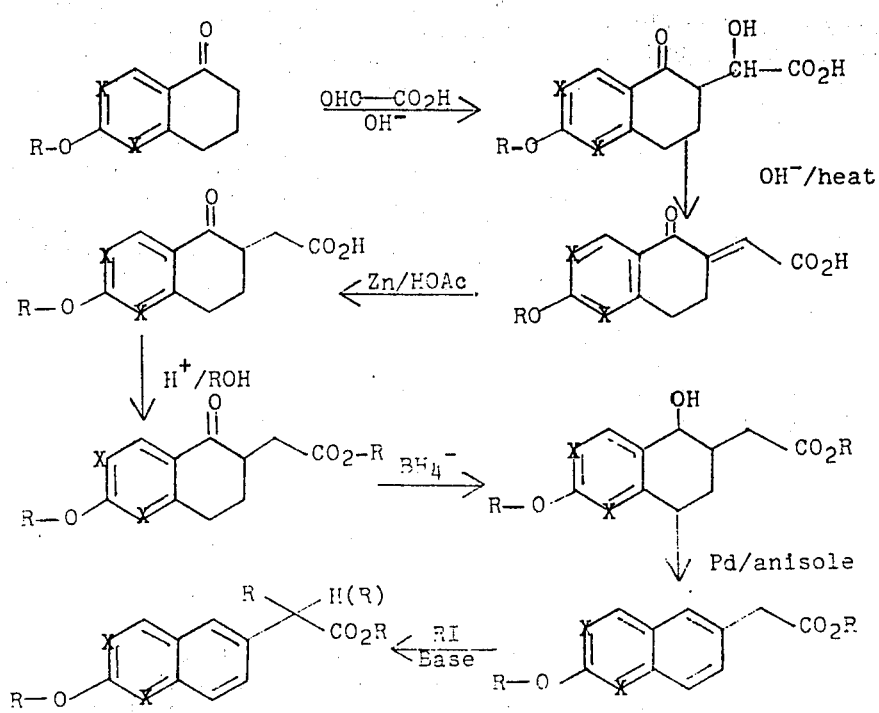

Scheme I wherein R and X are as previously defined.

5-Aza-6-loweralkoxytetralone (Tetrahedron Letters No. 1, pp. 87–90, 1966) and 7-aza-6-loweralkoxytetralone (Tetrahedron Letters No. 9, 623, 1975) are suitable precursors for initiating the above indicated reaction Scheme I. In accordance with Scheme I 7-aza-6-methoxytetralone is reacted with glyoxylic acid to provide 7-aza-2-carboxyhydroxymethyl-6-methoxy-1-tetralone and this compound is dehydrated by heating in base to provide 7-aza-6-methoxy-α-carboxymethylidene-1-tetralone. This latter tetralone is reduced with zinc/acetic acid to provide 7-aza-2-carboxymethyl-6-methoxy-1-tetralone and acid catalysed esterification with methanol and sulfuric acid provides 7-aza-6-methoxy-2-methoxycarbonylmethyl-1-tetralone. 7-Aza-6-methoxy-2-methoxycarbonylmethyl-1-tetralone to methyl 8-hydroxy-3-methoxy-5,6,7,8-tetrahydro-2-azanaphthalene-7-acetate by reaction with sodium borohydride and reaction of this product with Pd(C)/anisole provides methyl 3-methoxy-2-azanaphthalene-7-acetate which is alkylated with methyl iodide and base to provide methyl 3-methoxy-2-azanaphthalene-7-α-methylacetate and hydrolysis of this ester provides 3-methoxy-2-azanaphthalene-7-α-methylacetic acid.

An alternate and preferred method for preparing preferred compounds of the present invention is set out in Scheme II.

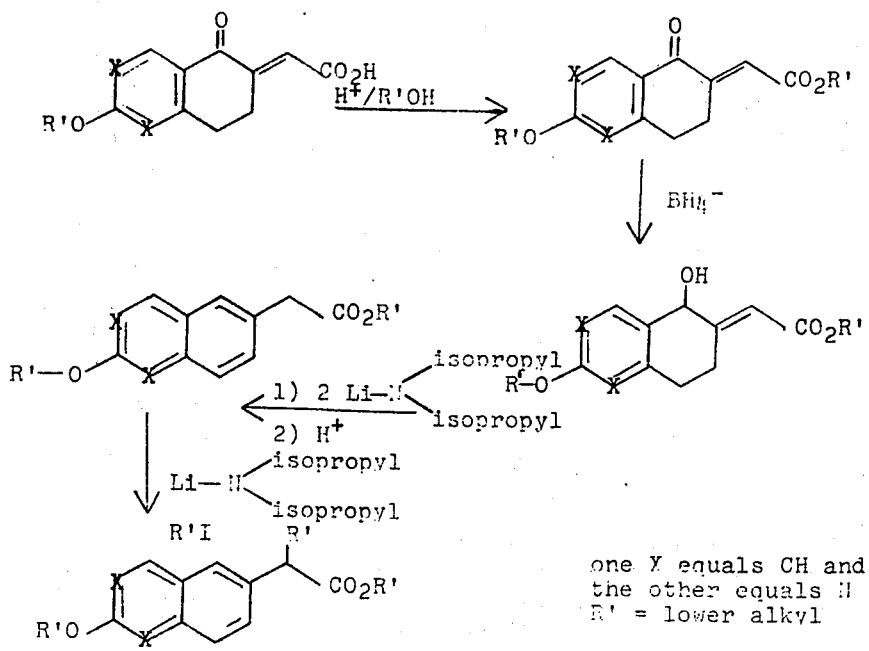

one Y equals CH and the other equals N
R' = lower alkyl

Scheme II

A preferred compound is obtained by acid catalysed esterification of 7-aza-6-methoxy-α-carboxymethylidene-1-tetralone with methanol. The resulting ester is reduced to 8-hydroxy-3-methoxy-5,6,7,8-tetrahydro-7-methoxycarbonylmethylidene-2-azanaphthalene which in turn is reacted with 2-equivalents of lithium diisopropylamine in tetrahydrofuran at −78° C. Following hydrolysis and acetic acid catalyzed dehydration of the resultant allylic alcohol to the azanaphthalene derivative, further treatment with lithium diisopropylamine, followed by alkylation with methyl iodide provides methyl 3-methoxy-2-azanaphthalene-7-α-methylacetate which is hydroylsed to 3-methoxy-2-azanaphthalene-7-α-methyl acetic acid. This acid is conveniently resolved into the d and l optical isomers by mixing a hot solution of 7.15 parts of the above acid in 20 parts by volume of methanol and 5 parts by volume of acetone and 1.5 parts of cinchonidine in 15 parts by volume of methanol and 10 parts by volume of acetone and then cooling the resulting solution. A salt precipitates upon cooling and this salt is filtered and crystallized from methanol-acetone and the free acid is liberated from the salt by shaking with a mixture of dilute hydrochloric acid and benzene. Evaporation of the benzene layer and crystallization of the residue from acetone-hexane provides d-α-methyl-2-azanaphthalene-7-α-methylacetic acid, the d enantiomer. Acidification of the mother liquor from the cinchonidine salt solution provides the l enantiomer 1-3-methoxy-2-azanaphthalene-7-α-methylacetic acid.

Anti-inflammatory utility of the instant compounds is provided by the results of a standardized test for their capacity to inhibit the edema induced in rats by injection of Mycobacterium butyricum. The procedure, which is similar to one described by Pearson et al. in Arthritis Rheumat., 2, 440 (1959), follows. Intact male Sprague-Dawley rats (60–70 grams) are randomized in groups of 12, one group for each compound to be tested plus one group to serve as controls. Each animal is injected intradermally (without any anesthesia) on the base of the tail with 0.6 mg. of dry heat-killed *Mycobacterium butyricum* (Difco 0640-33) suspended in 0.05 ml. of paraffin oil containing 2% digitonin whereupon the prescribed dose of compound, initially 10 mg/kg per day, dissolved or suspended in a vehicle consisting of 0.2 ml of either corn oil or a mixture of 20 ml of aqueous 0.85 sodium chloride with 1 drop of polysorbate 80, is intragastrically or subcutaneously administered. Administration thus of compound is repeated daily for the next 18 consecutive days. The control group is identically and concurrently administered vehicle alone. On the 20th day, the rats are sacrificed and the total volume of each pair of hind feet is measured in arbitrary units. A compound is considered antiinflammatory if the average volume (T) of the hind feet in the group treated therewith is significantly ($P = 0.05$) less than the corresponding value (C) for the control group. Hydrocortisone administered intragastrically has an $ED_{50}$ of approximately 7.0 mg/kg/day in this test. Dl 3-methoxy-2-azanaphthalene-7-α-methylacetic acid has an $ED_{50}$ of about 5.0 mg/kg/day in the above test.

Those skilled in the art will recognize that observations of acitivity in standardized tests for particular biological effects are fundamental to the development of valuable new drugs, both veterinary and human.

The compounds herein described can be combined with pharmaceutically acceptable carriers to provide novel pharmaceutical compositions.

The following examples are presented to further illustrate the present invention. They should not be construed as limiting it either in scope or in spirit. In these examples quantities are indicated in parts by weight unless parts by volume are specified, and temperatures are indicated in degrees Centigrade (° C).

EXAMPLE 1

To 5 parts of 7-aza-6-methoxy-1-tetralone in 50 parts by volume of methanol is added 3.0 parts of glyoxylic acid hydrate followed by 30 parts by volume of 5% aqueous sodium hydroxide and the reaction mixture is stirred at room temperature for 4 hours. Sufficient acetic acid is added to lower the pH of the solution to about 5. The solution is then extracted 6 times with ethyl acetate. The combined extracts are filtered and dried over anhydrous sodium sulfate. Removal of the solvent provides 7-aza-2-carboxyhydroxymethyl-6-methoxy-1-tetralone, melting at 165°–166° C. This compound has the following structural formula

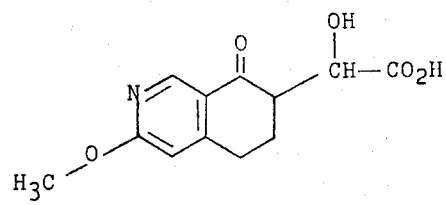

Continued heating on a steam bath for 2½ hours followed by isolation of the acid provides 7-aza-6-methoxy-2-carboxymethylidene-1-tetralone melting at 221°–222° C and having the following structural formula

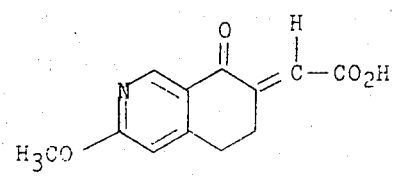

0.5 Part of this compound in 16 parts by volume of acetic acid, 8 parts by volume of water and 0.3 part of zinc dust is refluxed for 0.5 hour. The solution is cooled and the zinc is filtered. The volume of the filtrate is reduced to 10–15 parts by volume and to this concentrate is added 30 parts by volume of water. Cooling provides crystals of 7-aza-2-carboxymethyl-6-methoxy-1-tetralone, melting at 174°–176° C. This compound has the following structural formula.

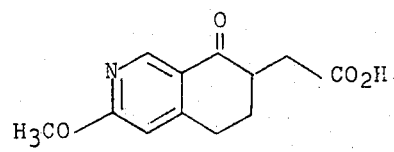

2.3 Parts of this compound in 50 parts by volume of methanol is esterified by diazomethane generated from 10 parts of nitrosomethylurea in 30 parts by volume of potassium hydroxide and 100 parts by volume of ether. The solution is allowed to set for 0.5 hours at room temperature and it is filtered. The solvent is reduced and upon cooling needles of 7-aza-6-methoxy-2-methoxycarbonylmethyl-1-tetralone, melting at 107–108.5° C. This compound has the following structural formula.

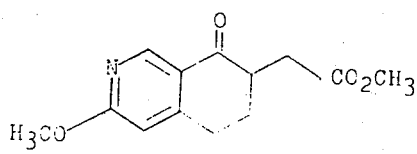

Alternatively, 7-aza-6-methoxy-2-carboxymethylidene-1-tetralone is esterified by acid catalysed reaction with methanol to provide 7-aza-6-methoxy-2-methoxycarbonylmethylidene-1-tetralone, melting at 111°–112° C. This compound has the following structural formula

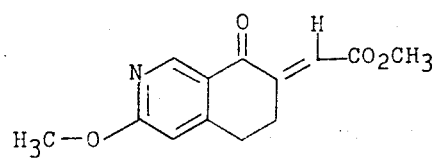

1 Part of this compound in 250 parts by volume of ethanol is catalytically reduced over 0.1 part of 5% Pd/C at 54.9 p.s.i. at room temperature to provide upon isolation 7-aza-6-methoxy-2-methoxycarbonylmethyl-1-tetralone.

To 4.05 parts of 7-aza-6-methoxy-2-methoxycarbonylmethyl-1-tetralone in 100 parts by volume of cold methanol is added in portions a total of 1.4 parts of sodium borohydride. The solution is warmed to room temperature and acetone is added. The solution is then reduced to ¼ its volume and precipitation occurs upon the addition of water. The precipitate is crystallized from ethanol to provide methyl 8-hydroxy-3-methoxy-5,6,7,8-tetrahydro-2-azanaphthalene-7-acetate, melting at 92°–96° C. This compound has the following structural formula.

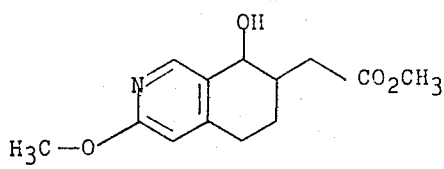

2.1 Parts of this compound is dissolved in 50 parts by volume of anisole containing 1.0 part of 10% Pd/C and the mixture is refluxed under nitrogen for 6 hours after which time 0.5 part of catalyst is again added and refluxing is continued. This process is repeated until a total of 10.5 parts of catalyst is added. The reaction mixture is cooled, filtered through Celite and washed 2 times with 5% sodium bicarbonate, and 2 times with saturated sodium chloride. Removal of the solvent provides an oil. Chromatography on silica gel using 10% ethyl acetate/benzene as eluent provides methyl 3-methoxy-2-azanaphthalene-7-acetate melting at 49.5°–51° C. This compound has the following structural formula

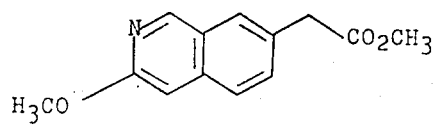

To 1 part of the above indicated ester in 30 parts by volume of tetrahydrofuran is added 1 part of lithium diisopropylamide and the mixture is cooled. To this mixture is added 0.5 parts of methyl iodide and the reaction mixture is stirred for 1 hour and allowed to warm to room temperature. The reaction is quenched with ethanol and then water. The reaction mixture is extracted with methylene chloride and the product isolated to provide methyl-3-methoxy-2-azanaphthalene-7-α-methylacetate having the following structural formula

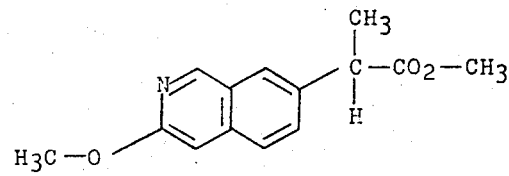

Repeating the -α-alkylation process provides methyl-3-methoxy-2-azanaphthalene-7-α,α-dimethylacetate, having the following formula

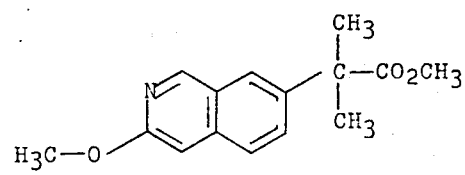

Alternatively the second alkylation may be conducted with 0.5 parts of ethyl iodide to provide methyl 3-methoxy-2-azanaphthalene-7-α-methyl-α-ethylacetate, having the following formula

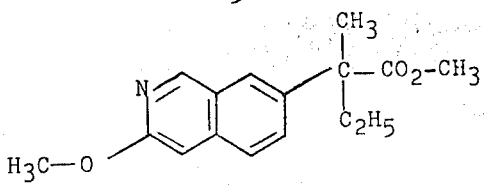

Hydrolysis of the above indicated esters by heating in alcoholic potassium hydroxide provides 3-methoxy-2-azanaphthalene-7-acetic acid, 3-methoxy-2-azanaphthalene-7-α-methylacetic acid, and 3-methoxy-2-azanaphthalene-7-α,α-dimethylacetic acid after acidification. In turn these acids are converted to ethyl esters by acid catalysed esterification with an excess of ethanol. Such esterification provides ethyl 3-methoxy-2-azanaphthalene-7-acetate, ethyl 3-methoxy-2-azanaphthalene-7-α-methylacetate, and ethyl 3-methoxy-2-azanaphthalene-7-α,α-dimethylacetate.

Optical Resolution: 3-Methoxy-2-azanaphthalene-7-α-methylacetic acid is reacted with cinchonidine to form the diastereo-isomer salts. Fractional crystallization followed by acid cleavage in dilute hydrochloric acid provides d and l 3-methoxy-2-azanaphthalene-7-α-methylacetic acid.

Refluxing 1 part of 3-methoxy-2-azanaphthalene-7-acetic acid in 25 parts by volume of 16% hydrobromic acid followed by extraction with methylene chloride and isolation provides 3-hydroxy-2-azanaphthalene-7-acetic acid, having the following formula

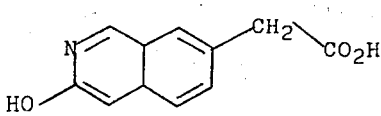

EXAMPLE 2

Following the procedures set out in Example 1 and using equivalent quantities 5-aza-6-ethoxytetralone (Tetrahedron Letters No. 1, pp. 87–90, 1966) is sequentially converted to 5-aza-2-carboxyhydroxymethyl-6-ethoxy-1-tetralone, 5-aza-6-ethoxy-2-carboxymethylidene-1-tetralone, 5-aza-6-ethoxy-2-methoxycarbonylmethyl-1-tetralone, methyl, methyl 5-hydroxy-2-ethoxy-5,6,7,8-tetrahydro-1-azanaphthalene-6-acetate, methyl-2-ethoxy-1-azanaphthalene-6-acetate, and methyl 2-ethoxy-1-azanaphthalene-6-α-methylacetate and 2-ethoxy-1-azanaphthalene-6-α-methylacetic acid, having the following formula

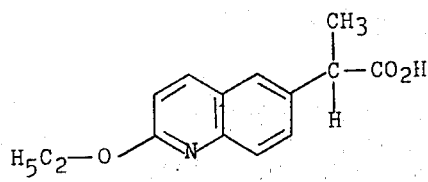

EXAMPLE 3

Reduction of 1 part of methyl-3-methoxy-2-azanaphthalene-7-α-methylacetic acid in 50 parts by volume ethyl ether containing 1 part of lithium aluminum hydride followed by quenching of the reaction with ethyl acetate, washing with saturated sodium chlorides, and isolation provides 7-(2-hydroxyethyl)-2-methoxy-1-azanaphthalene. This compound has the following structural formula

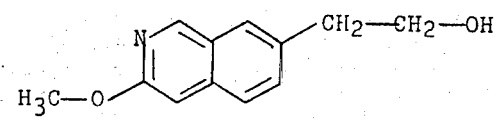

EXAMPLE 4

To 1 part of methyl 3-methoxy-2-azanaphthaleneacetate in 25 parts by volume of toluene at −78° C is slowly added 0.33 part of diisobutylaluminum hydride in toluene. The reaction is stirred for 1 hour and allowed to come to room temperature. The reaction is quenched with ethylacetate followed by ice water. The organic layer is washed with saturated sodium chloride, dried with anhydrous sodium sulfate, and 3-methoxy-2-azanaphthaleneacetaldehyde is isolated. This compound has the following structural formula

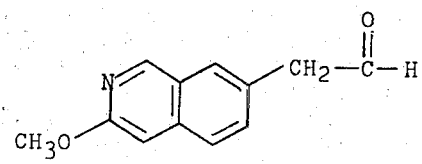

EXAMPLE 5

4.15 Parts of 7-aza-6-methoxy-2-methoxycarbonylmethylidene, melting at 111°–112° C and described in Example 1 is reduced by 0.4 part of sodium borohydride in 100 parts by volume of cold methanol to provide methyl 8-hydroxy-3-methoxy-5,6,7,8-tetrahydro-2-azanaphthalene-7-methylidenecarboxylate after isolation by the addition of water to the reaction mixture and filtration of the resulting precipitate. This compound has the following structural formula

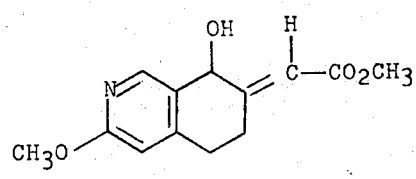

2.3 Parts of this hydroxy ester in 20 parts by volume of tetrahydrofuran is added slowly to a solution of lithium diisopropylamide prepared by reacting 2.3 parts of diisopropylamine with 13 parts by volume of 1.7 molar methyl lithium in ether in 35 parts by volume of tetrahydrofuran at −78° C and in an inert atmosphere. This reaction mixture may be treated by either of two procedures:

A. Quenched with acetic acid in ether to provide methyl 3-methoxy-2-azanaphthalene-7-acetate or B. By reaction of 0.5 parts of methyl iodide to provide methyl 3-methoxy-2-azanaphthalene-7-α-methylacetate as an oil.

Hydrolysis of 1.1 parts of this ester in 15 parts by volume of methanol containing aqueous potassium hydroxide by reflux for 1 hour, followed by cooling, acidification to pH 5, and extraction with ethyl acetate provides 3-methoxy-2-azanaphthalene-7-α-methylacetic acid upon evaporation of the ethyl acetate and recrystallization from methanol. This compound melts at 155.5°–156.5° C and has the following structural formula

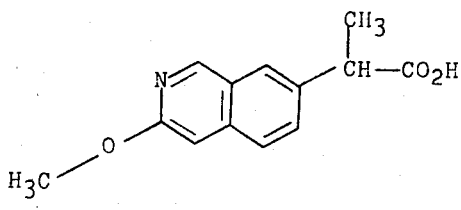

This acid is conveniently resolved into the d and l optical isomers by mixing a hot solution of 7.15 parts of the above acid in 20 parts by volume of methanol and 5 parts by volume of acetone and 1.5 parts of cinchonidine in 15 parts by volume of methanol and 10 parts by volume of acetone and then cooling the resulting solution. A salt precipitates upon cooling and this salt is filtered and crystallized from methanol-acetone and the free acid is liberated from the salt by shaking with a mixture of dilute hydrochloric acid and benzene. Evaporation of the benzene layer and crystallization of the residue from acetone-hexane provides d-α-methyl-2-azanaphthalene-7-α-methylacetic acid, the d enantiomer. Acidification of the mother liquor from the cinchonidine salt solution provides the l enantiometer, l-3-methoxy-2-azanaphthalene-7-α-methyl acetic acid.

EXAMPLE 6

11 Parts of 8-hydroxy-3-methoxy-5,6,7,8-tetrahydro-2-azanaphthalene-7-acetate described in Example 1 is added to 110 parts by volumn of sulfuric acid at room temperature and stirred for 15 minutes. 200 Parts of ice water are added and the solution is made basic with 300 parts by volume of aqueous ammonia. The solution is filtered through celite and then extracted three times with chloroform. Removal of the chloroform and crystallization from methanol provides 3-methoxy-7,8-dihydro-2-azanaphthalene-7-acetic acid, melting at 151–152° C and having the following formula

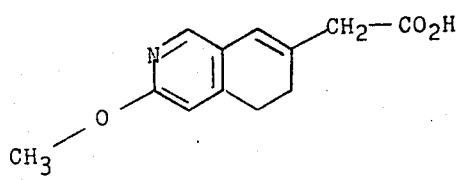

This compound is also an active anti-inflammatory agent, as is the alkylated derivative, 3-methoxy-7,8-dihydro-2-azanaphthalene-7-α-methylacetic acid.

What is claimed is:
1. A compound of the formula

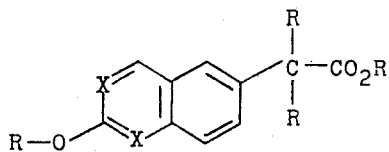

wherein each R independently represents hydrogen or lower alkyl having 1–7 carbon atoms and wherein one X represents N and the other X represents methylidyne.

2. A compound according to claim 1 having the formula

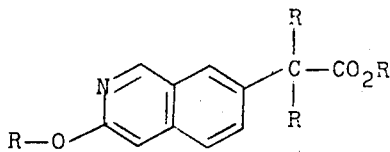

wherein each R independently represents hydrogen or lower alkyl having 1–7 carbon atoms.

3. A compound according to claim 1 having the formula

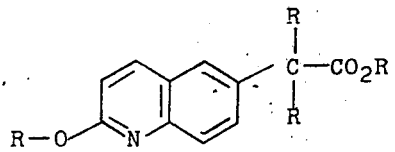

wherein each R independently represents hydrogen or lower alkyl having 1–7 carbon atoms.

4. A compound according to claim 1 having the formula

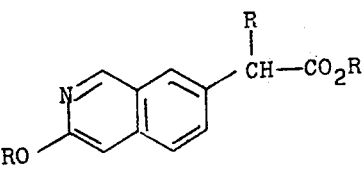

wherein each R independently is hydrogen or lower alkyl having 1–7 carbon atoms.

5. A compound according to claim 1 which is 3-methoxy-2-azanaphthalene-7-α-methylacetic acid.

6. A compound according to claim 1 which is 3-methoxy-2-azanaphthalene-7-acetic acid.

7. A compound according to claim 1 which is methyl 3-methoxy-2-azanaphthalene-7-acetate.

* * * * *